US006545148B2

(12) United States Patent
Xu et al.

(10) Patent No.: US 6,545,148 B2
(45) Date of Patent: *Apr. 8, 2003

(54) PROCESS FOR PREPARING CERTAIN SUBSTITUTED CAPROLACTAMS

(75) Inventors: David Daqiang Xu, Whippany, NJ (US); Wenming Liu, Parsippany, NJ (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/095,325

(22) Filed: Mar. 11, 2002

(65) Prior Publication Data

US 2002/0128474 A1 Sep. 12, 2002

Related U.S. Application Data

(60) Provisional application No. 60/275,099, filed on Mar. 12, 2001.

(51) Int. Cl.$^7$ ...................... C07D 223/12; C07D 223/10

(52) U.S. Cl. ........................................ 540/524; 540/526
(58) Field of Search ................................. 540/524, 526

(56) References Cited

U.S. PATENT DOCUMENTS

| 4,831,135 A | 5/1989 | Crews et al. ................ 540/526 |
| 6,239,127 B1 * | 5/2001 | Kinder, Jr. et al. ...... 514/212.03 |

FOREIGN PATENT DOCUMENTS

| WO | WO 00/29382 | 5/2000 |

* cited by examiner

*Primary Examiner*—Bruck Kifle
(74) *Attorney, Agent, or Firm*—Joseph J. Borovian

(57) ABSTRACT

The present invention relates to an improved process for preparing certain substituted caprolactam compounds which comprises acylating an aminocaprolactam compound with a lactone compound in the presence of a weak base and a polar, organic solvent, and hydrolyzing the resultant diamide compound in a mixture of solvents to obtain the desired caprolactam compound.

10 Claims, No Drawings

PROCESS FOR PREPARING CERTAIN SUBSTITUTED CAPROLACTAMS

This application claims the benefit of provisional application No. 60/275,099 filed Mar. 12, 2001, the contents of which are incorporated herein by reference.

The present invention relates to a process for preparing certain substituted caprolactams.

FIELD OF INVENTION

The present invention relates to the area of synthetic methodology and, more particularly, to a process for preparing certain substituted caprolactams.

BACKGROUND OF THE INVENTION

Marine organisms provide a potential source of biologically active compounds, including compounds which are potentially useful as anti-tumor agents. For example, U.S. Pat. No. 4,831,135 discloses certain bengamide compounds which were isolated by extraction from the Jaspidae marine sponge family native to the waters surrounding the Fiji islands and which exhibit anti-tumor, antibiotic and anthelmintic properties. In fact, the chemistry of Jaspidae sponges has been the subject of numerous publications over the last 10 years.

More recently, WO 00/29382 discloses certain analogs of the bengamides disclosed in the above-mentioned U.S. patent, which analogs are useful in treating various types of tumors. Although WO 00/29382 discloses a suitable process for preparing all of the analogs disclosed therein, their ever-growing importance has resulted in a need for a more practical and commercially acceptable synthesis.

SUMMARY OF THE INVENTION

The present invention relates to an improved process for preparing certain substituted caprolactams. The process of the present invention is believed to be more practical and commercially acceptable than the process disclosed in WO 00/29382 since it is carried out under more mild reaction conditions and results in an easier work-up of the desired compounds. More particularly, the process of the instant invention involves the acylation of an aminocaprolactam compound with a lactone compound in the presence of a weak base and a polar, organic solvent, and the hydrolysis of the 1,3-dioxane group of the resulting diamide compound to obtain the desired substituted caprolactam compound.

DETAILED DESCRIPTION OF THE INVENTION

The present invention relates to an improved process for preparing certain substituted caprolactams of formula I:

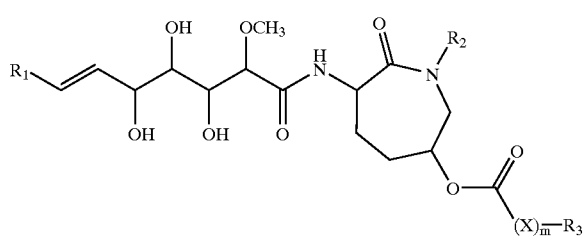

where
$R_1$ is $(C_{1-6})$alkyl or $(C_{3-6})$cycloalkyl;

$R_2$ is hydrogen or $(C_{1-6})$alkyl;

X is $(C_{1-12})$ alkylene; $(C_{2-12})$ alkenylene; or $(C_{2-12})$ alkynylene;

m is 0 or 1; and $R_3$ is $(C_{3-8})$cycloalkyl; or an aromatic ring system selected from II, III, IV and V:

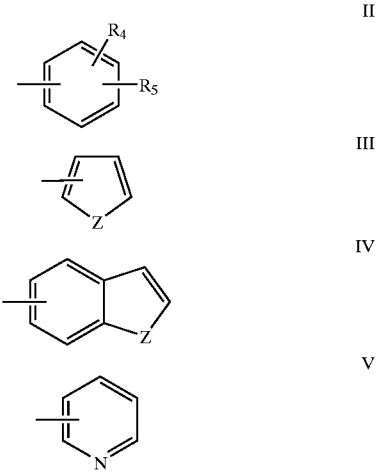

where
$R_4$ is hydrogen, chloro, or methoxy;
$R_5$ is hydrogen, chloro, $(C_{1-18})$alkyl or $(C_{1-18})$alkoxy;
and Z is oxygen, sulfur, N—H, or N—CH$_3$;

or a pharmaceutically acceptable acid addition salt thereof, where possible. More particularly, the substituted caprolactam compounds of formula I are prepared by a two-step process as depicted below:

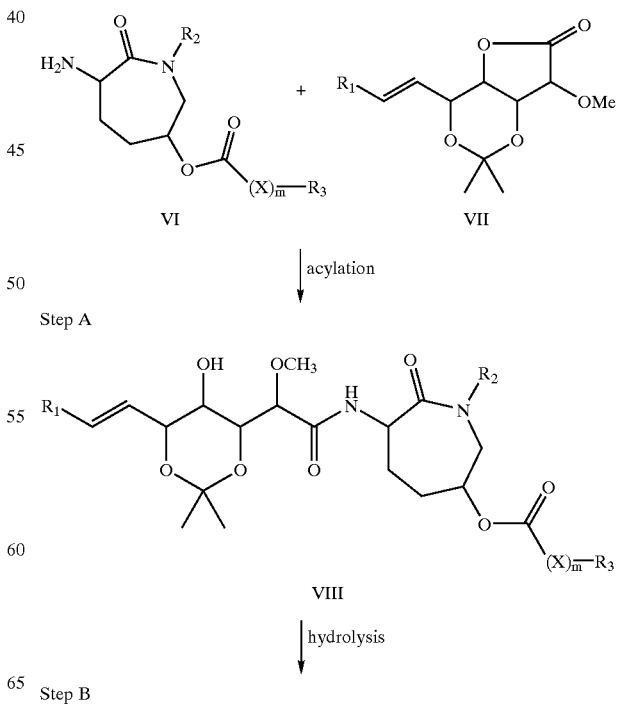

Step A

Step B

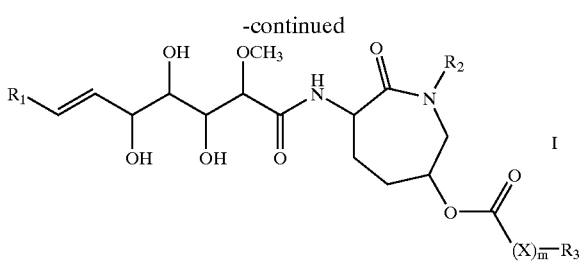

where each $R_1$, $R_2$, X, m and $R_3$ is as defined above.

s to the individual steps, Step A involves the acylation of an aminocaprolactam compound of formula VI, or an acid addition salt thereof, with a lactone compound of formula VII to obtain a diamide compound of formula VIII. The acylation is conducted in the presence of: 1) a weak base, preferably a carboxylate salt such as sodium 2-ethylhexanoate, and 2) a polar, organic solvent, preferably a cyclic ether such as tetrahydrofuran, at a temperature of between 0° C. and 50° C., preferably at 25° C., for a period of between 1 hour and 7 days, preferably for 20 hours.

Step B concerns the hydrolysis of the 1,3-dioxane group common to a diamide compound of formula VIII, to obtain the desired substituted caprolactam compound of formula I. The hydrolysis is typically carried out by dissolving the diamide in a mixture of solvents consisting of 1) a protic acid, preferably an organic acid such as trifluoroacetic acid, or an inorganic acid such as hydrochloric acid; 2) a protic solvent, preferably water, and 3) an inert organic solvent, preferably a cyclic ether such as tetrahydrofuran, at a temperature of between 0° C. and 50° C. for a period of between 1 hour and 5 hours.

The aminocaprolactam compounds of formula VI and the lactone compounds of formula VII may be prepared as described in WO 00/29382. As indicated above, an acid addition salt of a compound of formula VI may be utilized in Step A. For example, the compound of Example 1g) of WO 00/29382 can be reacted with HCl to form the corresponding hydrochloride salt form of the compound of Example 1h) of WO 00/29382.

Although the diamide compound that is obtained in Step A described above may, if desired, be purified by conventional techniques such as recrystallization, the crude diamide compound is advantageously employed in Step B described above without purification.

The free base of the compound of formula I may, if desired, be converted into the acid addition salt form, where possible. The acid addition salts of the compounds of formula I may be those of pharmaceutically acceptable organic or inorganic acids. Although the preferred acid addition salts are those of hydrochloric and methanesulfonic acid, salts of sulfuric, phosphoric, citric, fumaric, maleic, benzoic, benzenesulfonic, succinic, tartaric, lactic and acetic acid are also contemplated. Such salts may be obtained by reacting the free base of a compound of formula I with the corresponding acid to obtain the desired acid addition salt form.

As is evident to those skilled in the art, the substituted caprolactam compounds of formula I contain asymmetric carbon atoms. It should be understood, therefore, that the individual stereoisomers are contemplated as being included within the scope of the invention.

Preferred substituted caprolactams which may be prepared by the process of this invention are those of formula I where $R_1$ is $(C_{1-6})$alkyl;
$R_2$ is hydrogen or $(C_{1-4})$alkyl;
X is $(C_{1-6})$alkylene or $(C_{2-6})$alkynylene;
m is 0 or 1; and
$R_3$ is $(C_{3-8})$cycloalkyl; or an aromatic ring system selected from II, III, IV and V where
$R_4$ is hydrogen, chloro, or methoxy; and
$R_5$ is hydrogen, chloro, $(C_{1-18})$alkyl or $(C_{1-18})$alkoxy; and Z is oxygen, sulfur, N—H, or N—CH$_3$;

or a pharmaceutically acceptable acid addition salt thereof, where possible.

More preferred substituted caprolactams which may be prepared by the process of this invention are those of formula I where $R_1$ is i-propyl or t-butyl;
$R_2$ is hydrogen or methyl;
m is 0 or 1;
X is $(C_{1-6})$ alkylene; and
$R_3$ is $(C_{5-7})$cycloalkyl; or an aromatic ring system selected from IIa and V:

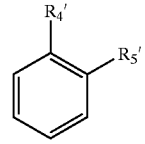

IIa

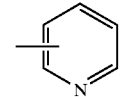

V where
$R_4'$ is in the meta position and is hydrogen or chloro; and
$R_5'$ is in the para position and is hydrogen, chloro, $(C_{1-18})$alkyl or $(C_{1-18})$alkoxy;

or a pharmaceutically acceptable acid addition salt thereof, where possible.

Even more preferred substituted caprolactam compounds which may be prepared by the process of this invention are those of formula I where $R_1$ is i-propyl or t-butyl;
$R_2$ is hydrogen or methyl;
m is 0 or 1;
X is methylene or ethylene; and
$R_3$ is $(C_{5-7})$cycloalkyl, phenyl, 3,4-dichlorophenyl, 4-methoxyphenyl, 4-n-decylphenyl, 4-n-decyloxyphenyl or 3-pyridyl;
with the proviso that when m is 0, $R_3$ is $(C_{5-7})$ cycloalkyl, 4-n-decylphenyl or 4-n-decyloxyphenyl;

or a pharmaceutically acceptable acid addition salt thereof, where possible.

The following examples are for purposes of illustration only and are not intended to limit in any way the scope of the instant invention.

EXAMPLE 1

(6E)-6,7,8,9-tetradeoxy-8,8-dimethyl-2-O-methyl-3, 5-O-(1-methylethylidene) -gulo-non-6-enonic acid lactone Following essentially the procedures of Examples 1a)-1e) of WO 00/29382, the title compound is obtained as a white crystalline solid.

EXAMPLE 2

(3S, 6R)-3-(tert-butoxycarbonyl)aminohexahydro-6-(cyclohexanecarbonyl)oxy-2H-azepin-2 -one.

Following essentially the procedures of Examples 1f) and 1g) of WO 00/29382, the title compound is obtained as a white solid.

EXAMPLE 3

(2R, 3R, 4S, 5R, 6E)-3,4,5-trihydroxy-2-methoxy-8,8-dimethyl-N-[(3S,6R)-hexahydro-2-oxo-6-(cyclohexylcorbonyl)oxy-2H-azepin-3-3-yl]non-6-enamide.

a) Preparation of (2R, 3R, 4S, 5R, 6E)-3,5-(methylethylidene)-3,4,5-trihydroxy-2-methoxy-8,8-dimethyl-N-[(3S,6R)-hexahydro-2-oxo-6-(cyclohexylcarbonyl)oxy-2H-azepin-3-yl]non-6-enamide.

To a stirred solution of ethyl acetate (3 L) and HCl gas (225 g, 6.2 mol) at room temperature is added, portionwise, 300 g (846 mmol) of the compound of Example 2. The reaction is stirred at room temperature for 6 hours. The resulting precipitate is filtered and the solid is washed with ethyl acetate (1.2 L). The solid is dried to give 246 g (98%) of (3S, 6R)-3-aminohexahydro-6-cyclohexanecarbonyl)oxy-2H-azepin-2-one.HCl which is used directly in the next step. A solution consisting of 100 g (352 mmol) of the compound of Example 1, 112.5 g (387 mmol) of 3S, 6R)-3-aminohexahydro-6-(cyclohexanecarbonyl)oxy-2H-azepin-2-one.HCl, sodium 2-ethylhexanoate (116 g, 700 mmol) and tetrahydrofuran (1.75 L) is stirred at room temperature for 20 hours. Water (350 mL) is then added to the mixture. After stirring for an additional 30 minutes, heptane (3.5 L) is added. The mixture is then stirred for 3 hours, then cooled to 2° C. and then stirred for an additional 2 hours. The mixture is filtered through a polypropylene filter. The solid that remains is washed with water (200 mL) and heptane (800 mL). The solid is then dried to give 166 g (88%) of the desired compound as a white solid.

b) Preparation of the Title Compound.

To a stirred solution of trifluoroacetic acid (10 ml), tetrahydrofuran (10 ml) and water (5 ml) at 0° C. is added, in one portion, 3.8 g (7.1 mmol) of the compound prepared in a) above. The reaction is stirred at 0° C. for 30 minutes, concentrated via rotary evaporation (bath temperature <20° C), mixed with saturated $NH_4HCO_3$ (5 mL) and stirred for 15 minutes. The mixture is concentrated in vacuo and chromatographed (2% methanol-$CH_2Cl_2$) to give a white solid with $H_2O$ solubility of 3.7 mg/mL. This material is further purified using preparative hplc (reverse phase eluted with 90% $CH_3CN$-water) to give 2.9 g (82.4%) of the title compound as a white solid, m.p. 79–80° C.

b[1]) Alternate Preparation of the Title Compound.

To a cooled (22° C.) solution of tetrahydrofuran (100 mL) and 1N hydrochloric acid (200 mL) is added 10 g (28.2 mmol) of the compound of Example 2. The resultant mixture is stirred for 3 hours at 22° C., after which time it is cooled to 5° C. The reaction mixture is then neutralized with an aqueous 5N sodium hydroxide solution (40 mL) to a pH of 7. Sodium chloride (77 g, 1.32 mol) is then added to the resultant mixture, after which time it is stirred for 30 minutes at 22° C. The resultant product is then extracted into ethyl acetate (100 mL) and the solvents are removed under vacuum. The residue is then re-dissolved in tert-butyl methyl ether (40 mL) at 50° C., crystallized from the solution at 20° C.-0° C., collected by filtration and washed with tert-butyl methyl ether (20 mL). After drying, 8 g of the crude product is obtained. The crude product is further purified by recrystallization from a mixture of ethanol (10 mL) and water (40 mL) at 0° C. to give 7.2 g of the title compound as a white solid.

What is claimed is:

1. A process for preparing a caprolactam compound of formula I

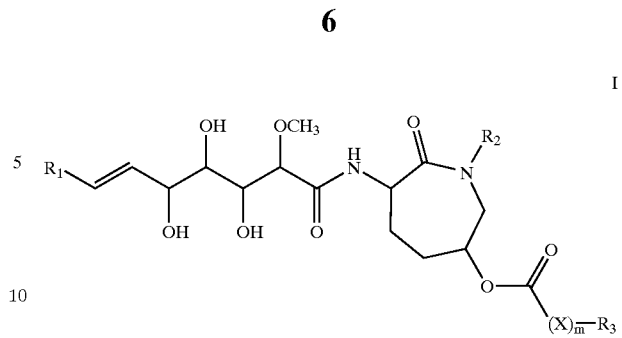

where $R_1$ is $(C_{1-6})$alkyl or $(C_{3-6})$cycloalkyl;

$R_2$ is hydrogen or $(C_{1-6})$alkyl;

X is $(C_{1-12})$ alkylene; $(C_{2-12})$ alkenylene; or $(C_{2-12})$ alkynylene;

m is 0 or 1; and $R_3$ is $(C_{3-8})$cycloalkyl; or an aromatic ring system selected from II, III, IV and V:

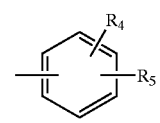

II

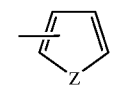

III

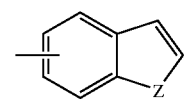

IV

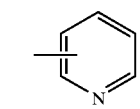

V where $R_4$ is hydrogen, chloro, or methoxy;

$R_5$ is hydrogen, chloro, $(C_{1-18})$alkyl or $(C_{1-18})$alkoxy; and Z is oxygen, sulfur, N—H, or N—$CH_3$;

or a pharmaceutically acceptable acid addition salt thereof, where possible, which process comprises, in a first step, acylating an aminocaprolactam compound of formula VI

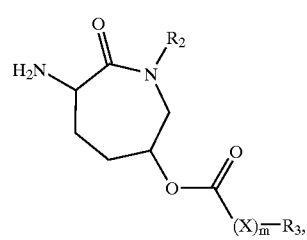

VI or an acid addition salt thereof, with a lactone compound of formula VII

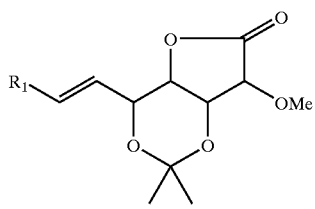

in the presence of: 1) a weak base; and 2) a polar organic solvent to obtain a diamide compound of formula VIII

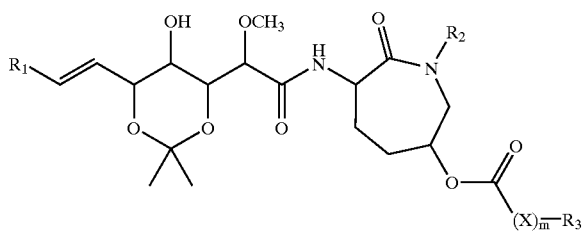

where each of $R_1$, $R_2$, X, m and $R_3$ is as defined above and, in a second step, hydrolyzing the diamide compound obtained in the first step by dissolving it in a mixture of solvents to obtain the desired caprolactam compound of formula I.

2. A process according to claim 1 wherein the acylation step is carried out in the presence of: 1) a carboxylate salt; and 2) a cyclic ether.

3. A process according to claim 2 wherein the acylation step is carried out in the presence of: 1) sodium 2-ethylhexanoate; and 2) tetrahydrofuran.

4. A process according to claim 3 wherein the acylation step is carried out at a temperature of between 0° and 50° C.

5. A process according to claim 1 wherein the hydrolysis step is carried out by dissolving the diamide compound obtained in the first step in a mixture of solvents consisting of: 1) a protic acid; 2) a protic solvent; and 3) an inert, organic solvent.

6. A process according to claim 5 wherein the mixture of solvents consists of: 1) an organic acid; 2) water; and 3) a cyclic ether.

7. A process according to claim 6 wherein the mixture of solvents consists of: 1) trifluoroacetic acid; 2) water; and 3) tetrahydrofuran.

8. A process according to claim 5 wherein the hydrolysis step is carried out at a temperature of between 0° and 50° C.

9. A process according to claim 5 wherein the mixture of solvents consists of: 1) an inorganic acid; 2) water; and 3) a cyclic ether.

10. A process according to claim 9 wherein the mixture of solvents consists of: 1) hydrochloric acid; 2) water; and 3) tetrahydrofuran.

* * * * *